(12) United States Patent
Neas et al.

(10) Patent No.: US 9,018,412 B2
(45) Date of Patent: Apr. 28, 2015

(54) α-KETO ALKYLPERACIDS AND METHODS FOR PRODUCING AND USING THE SAME (71) Applicant: CHD Bioscience, Inc., Fort Collins, CO (US)

(72) Inventors: Edwin D. Neas, Nunn, CO (US); John D. Skinner, Fort Collins, CO (US)

(73) Assignee: CHD Bioscience, Inc., Fort Collins, CO (US)

( * ) Notice: Subject to any disclaimer, the term of this patent is extended or adjusted under 35 U.S.C. 154(b) by 0 days.

(21) Appl. No.: 13/898,126

(22) Filed: May 20, 2013

(65) Prior Publication Data

US 2013/0251820 A1    Sep. 26, 2013

Related U.S. Application Data (63) Continuation of application No. 12/760,940, filed on Apr. 15, 2010, now Pat. No. 8,445,717, which is a continuation-in-part of application No. 12/618,605, filed on Nov. 13, 2009, now Pat. No. 8,426,634.

(60) Provisional application No. 61/199,944, filed on Nov. 20, 2008.

(51) Int. Cl.
*C07C 409/24* (2006.01)
*A01N 37/42* (2006.01)

(52) U.S. Cl.
CPC .............. *A01N 37/42* (2013.01); *C07C 409/24* (2013.01)

(58) Field of Classification Search
CPC .. C07C 409/26; C07C 407/003; C07C 51/412
See application file for complete search history.

(56) References Cited

U.S. PATENT DOCUMENTS

| | | | |
|---|---|---|---|
| 2,806,045 | A | 9/1957 | Gross |
| 3,169,986 | A | 2/1965 | Reginald et al. |
| 3,829,468 | A | 8/1974 | Serad et al. |
| 3,978,032 | A | 8/1976 | Manner |
| 4,004,977 | A | 1/1977 | Kato et al. |
| 4,008,175 | A | 2/1977 | Barter |
| 5,597,791 | A | 1/1997 | Richards et al. |
| 5,718,910 | A | 2/1998 | Oakes et al. |
| 6,325,968 | B1 | 12/2001 | Fricker et al. |
| 6,627,657 | B1 | 9/2003 | Hilgren et al. |
| 6,943,190 | B2 | 9/2005 | Fink et al. |
| 6,991,685 | B2 | 1/2006 | Kravitz et al. |
| 8,426,634 | B2 | 4/2013 | Neas et al. |
| 8,445,717 | B2 | 5/2013 | Neas et al. |
| 2001/0016604 | A1 | 8/2001 | Yu et al. |
| 2004/0176267 | A1 | 9/2004 | Hobson et al. |
| 2005/0197397 | A1 | 9/2005 | Martin |
| 2007/0048345 | A1 | 3/2007 | Huang et al. |
| 2007/0056904 | A1 | 3/2007 | Hogt et al. |
| 2007/0082832 | A1 | 4/2007 | DiCosimo et al. |
| 2007/0148214 | A1 | 6/2007 | Cullen et al. |
| 2007/0202069 | A1 | 8/2007 | Tamareselvy et al. |
| 2008/0233069 | A1 | 9/2008 | Tamareselvy et al. |
| 2009/0145859 | A1 | 6/2009 | Man et al. |
| 2010/0040608 | A1 | 2/2010 | Wahren-Herlenius et al. |
| 2010/0108942 | A1 | 5/2010 | Man et al. |
| 2010/0125104 | A1 | 5/2010 | Neas et al. |
| 2011/0117178 | A1 | 5/2011 | Junginger |
| 2011/0165261 | A1 | 7/2011 | Derby et al. |
| 2011/0301070 | A1 | 12/2011 | Ochomogo et al. |
| 2011/0305872 | A1 | 12/2011 | Li et al. |
| 2012/0021486 | A1 | 1/2012 | Dinu et al. |
| 2012/0213835 | A1 | 8/2012 | Neas et al. |
| 2013/0224307 | A1 | 8/2013 | Neas et al. |
| 2013/0330397 | A1 | 12/2013 | Neas et al. |

FOREIGN PATENT DOCUMENTS

| | | |
|---|---|---|
| EP | 0320219 | 6/1989 |
| WO | WO 91/13058 | 9/1991 |
| WO | WO 93/01716 | 2/1993 |
| WO | WO 2006/093792 | 9/2006 |
| WO | WO 2007/018923 | 2/2007 |
| WO | WO 2010/059531 | 5/2010 |
| WO | WO 2011/129829 | 10/2011 |
| WO | WO 2012/112951 | 8/2012 |

OTHER PUBLICATIONS

Wuebbles et al. (Journal of Geophysical Research, 2001, 106, 14551).*
Bunton (1949) Nature 163:444 "Oxidation of α-Diketones and α-Keto-Acids by Hydrogen Peroxide".
Cooper, et al. (1983) Chem. Rev. 83:321-358 "Synthesis and Properties of the α-Keto Acids".
Desagher et al. (1997) The Journal of Neuroscience 17(23):9060-9067 "Pyruvate Protects Neurons against Hydrogen Peroxide-Induced Toxicity".
Estes et al. (2010) Expert Rev Anti Infect Ther 8(3):325-338 "Present and future therapeutic strategies for melioidosis and glanders" doi:10.1586/eri.10.4.
European Search Report for 09828061.3 mailed Sep. 24, 2012, 7 pages.
Fink (2007) Current Drug Targets 8:515-518 "Ethyl Pyruvate: A Novel Treatment for Sepsis".
Fink (2007) J Intern Med 261:349-362 "Ethyl pyruvate: a novel anti-inflammatory agent".
Greenspan (1947) Industrial and Engineering Chemistry 39:847-848 "Oxidation Reactions with Aliphatic Peracids" XP-002683108.
Hanson (1987) Department of Biological Sciences 64(7):591-595 "Decarboxylation of α-Keto Acids".
Holleman (1904) Recl. Tray. Chim. Pays-bas Belg. 23 (English Abstract).

(Continued)

*Primary Examiner* — Rosalynd Keys
*Assistant Examiner* — Jennifer C Sawyer
(74) *Attorney, Agent, or Firm* — Volpe and Koenig, P.C.

(57) ABSTRACT

The present invention provides α-keto alkylperacids and methods for producing and using the same. In particular, α-keto alkylperacids are useful as antimicrobial agents.

20 Claims, 4 Drawing Sheets

(56) References Cited

OTHER PUBLICATIONS

International Search Report for PCT/US09/64450 dated May 31, 2010, 5 pages.

International Search Report for PCT/US10/31245 dated Jan. 21, 2011, 5 pages.

International Search Report for PCT/US12/25736 dated May 29, 2012, 1 page.

Lever and Mackenzie (2007) BMJ 335:879-883 "Sepsis: definition, epidemiology, and diagnosis".

Miyaji et al. (2003) Kidney International 64:1620-1631 "Ethyl pyruvate decreases sepsis-induced acute renal failure and multiple organ damage in aged mice".

Nath et al. (1995) The American Physiological Society C227-C236 "α-Ketoacids scavenge $H_2O_2$ in vitro and in vivo and reduce menadione-induced DNA injury and cytotoxicity".

Neas et al. (2013) Power Point Presentation presented on Jan. 3, 2013 for U.S. Appl. No. 12/618,605 "CHD Bioscience: Answers for infectious disease: CHD Meeting with USPTO" 31 slides.

Panda and Patnaik (2001) Bull. Korean Chem. Soc. 22(8):909-913 "Peroxy Acid Oxidations: a Kinetic and Mechanistic Study of Oxidative Decarboxylation of α-Keto Acids by Peroxomonophosphoric Acid".

Swern (1948) Eastern Regional Research Laboratory 1-68 "Organic Peracids".

Vlachou and Berth-Jones (2007) Journal of Dermatological Treatment 18:175-177 "Nail psoriasis improvement in a patient treated with fumaric acid esters".

Vlessis et al. (1990) Biochemical and Biophysical Research Communications 170(3):1281-1287 "Importance of Spontaneous α-Ketoacid Decarboxylation in Experiments Involving Peroxide".

Wang et al. (1999) Science 285:248-251 "HMG-1 as a Late Mediator of Endotoxin Lethality in Mice".

International Search Report for PCT/US13/65782 dated Feb. 19, 2014, 32 pages.

North Cell Pharm pamphlet "Effect of Alpha Keto Acids Including Sodium Pyruvate on Reducing and Regulating the Inflammatory Agents Needed in the Healing of Infected and Non-Infected Wounds" [retrieved on Mar. 17, 2014 from http://www.northcellpharma.com/NCP_Research_Devel_Data.pdf.

* cited by examiner

| | Log Reduction of Bacteria By Disinfectant | | | | | | |
|---|---|---|---|---|---|---|---|
| TEST METHOD | Spray | Spray | Spray | Immersion | Immersion & ASTM-E2107 | Immersion | AOAC 966.04 |
| | *Escheria coli* | MRSA | *Candida albicans* | *Clostridium sporogenes* | *Clostridium difficile* | *Bacillus cereus* | *Bacillus Subtilis* |
| Pyruvic Acid | ≥6.0 | ≥8.0 | ≥6.0 | | | ≥1.5 | |
| Alpha Keto Butyric Acid | ≥6.0 | ≥6.0 | | | | | |
| Alpha Keto Valeric Acid | ≥6.0 | ≥5.7 | | | | | |
| Peroxy Pyruvic Acid | ≥6.0 | ≥6.0 | ≥6.0 | ≥6.0 | ≥6.0 | ≥6.0 | ≥5.0 |
| Peroxy Alpha Keto Butyric Acid | | | | | ≥6.0 | | ≥5.0 |
| Peroxy Alpha Keto Valeric Acid | | | | | ≥6.0 | | |

Figure 4

α-KETO ALKYLPERACIDS AND METHODS FOR PRODUCING AND USING THE SAME

CROSS-REFERENCE TO RELATED APPLICATIONS

This application is a continuation of U.S. patent application No. 12/760,940 (now U.S. Pat. No. 8,445,717), filed Apr. 15, 2010 by Edwin D. Neas et al. and entitled "Alpha-keto Alkylperacids and Methods For Producing and Using the Same". which is a continuation-in-part of U.S. patent application No. 12/618,605 (now U.S. Pat. No. 8,426,634), filed Nov. 13, 2009, which claims the priority benefit of U.S. Provisional Patent Application No. 61/199,944, filed Nov. 20, 2008, all of which are incorporated herein by reference in their entirety.

FIELD OF THE INVENTION

The present invention relates to α-keto alkylperacids and methods for producing and using the same.

BACKGROUND OF THE INVENTION

Human and mammalian health is impacted by the spread of microbial organisms such as viruses, bacteria, and fungi. Microbial organisms continue to cause a variety of sicknesses and ailments. In the wake of widespread microbial organism infections, the public has become even further concerned with sanitization, both of person and property. Consequently, there has been an extensive research on the development of suitable antimicrobial compositions, in particular of antimicrobial compositions that provide immediate and residual kill of microbial organisms.

Currently, there exist several compositions and methods for reducing and/or eliminating microbial organisms from various surfaces. Conventional antimicrobial cleansing products such as hard surface cleaners and surgical disinfectants are typically formulated to provide bacteria removal during washing. Only a few such products have been shown to provide a residual effectiveness against Gram-positive bacteria; however, even such compositions provide only limited residual effectiveness against Gram-negative bacteria. By "residual effectiveness", it is meant that the subject antimicrobial controls microbial growth on a substrate by either preventing growth of microbes or engaging in continuous kill of microbes for some period of time following the washing and/or rinsing process.

Furthermore, many conventional antimicrobial compositions have unpleasant odor or are chemically harsh and can cause irritation. Moreover, most conventional antimicrobial compositions are relatively ineffective against vegetative bacteria that are "dormant." Vegetative bacteria are bacteria or microoganisms that can grow and reproduce in rich, moist soil where many nutrients are available. The actively growing bacteria in these conditions are referred to as "vegetative cells." Many types of bacteria and fungi can flourish under these conditions. Some examples of bacteria and fungi that can actively reproduce in this kind of soil are *Bacillus, Streptomyces, Pseudomonas, Micrococcus, Mycobacterium*, and *Clostridium. Mycobacterium tuberculosis* can cause the disease tuberculosis, and *Colstridium botulinum* can cause botulism poisoning.

When soil nutrients or moisture are depleted, bacteria from the genus of *Bacillus* and *Clostridium* produce an endospore inside each vegetative cell. Once the vegetative cell (active bacteria) no longer has enough nutrients or moisture to survive, it releases the endospore. The endospore can remain viable for very long periods. When the right conditions return for growth, the endospore creates another vegetative cell, and the bacteria becomes active again. Some fungi produce spores in a similar fashion.

Therefore, there is a need for antimicrobial compositions that are effective against vegetative microbial organisms. There is also a need for antimicrobial compositions that do not have unpleasant odor.

SUMMARY OF THE INVENTION

Some aspects of the invention provide α-keto alkylperacids and methods for producing and using the same. Such methods typically comprise contacting an α-keto alkylcarboxylic acid or a salt thereof with an oxidizing agent without any significant stirring and under conditions sufficient to produce the α-keto alkylperacid. While a variety of oxidizing agents can be used in such methods, typically the oxidizing agent comprises hydrogen peroxide, barium peroxide, sodium carbonate peroxide, calcium peroxide, sodium perborate, lithium peroxide, magnesium peroxide strontium peroxide, zinc peroxide, potassium superoxide, or a mixture thereof. In some embodiments, the reaction temperature is about 10° C. or less. In other embodiments, the reaction temperature ranges from about −30° C. to about 10° C.

Methods of the invention can be used to produce a wide variety of α-keto alkylperacids. In some aspects of the invention, the α-keto alkylperacid is of the formula:

or a salt thereof,
where R is alkyl of at least two carbon atoms.

In some embodiments, R is $C_2$-$C_{20}$ alkyl. Within these embodiments, in some instances, R is $C_2$-$C_{10}$ alkyl. In some cases, R is selected from the group consisting of ethyl, isopropyl, propyl, butyl, isobutyl, sec-butyl, pentyl, isopentyl, neopentyl, and n-hexyl.

Other aspects of the invention provide methods for reducing the amount of microbe on a surface. Such methods typically include contacting the surface with an antimicrobial solution comprising an effective amount of a compound of Formula I.

In some embodiments, the microbe comprises vegetative bacteria. Within these embodiments, in some instances the microbe comprises bacterial spores, mycobacteria, gram-negative bacteria, vegetative gram-positive bacteria, or a combination thereof.

Still in other embodiments, the antimicrobial solution further comprises hydrogen peroxide.

Yet in other embodiments, the antimicrobial solution comprises at least 40 ppm of the compound of Formula I.

Still other aspects of the invention provide methods for reducing the number of infectious vegetative bacteria on a substrate. Such methods include contacting the substrate with an antimicrobial solution comprising an effective amount of a compound of Formula I.

Yet other aspects of the invention provide methods for preventing and/or reducing bacteria-related diseases in a mammal that result from the mammal's contact with a bacteria-infected substrate. Such methods can include contacting the substrate with a composition comprising of a compound of Formula I.

Other aspects of the invention provide antimicrobial products comprising a compound of Formula I.

In some embodiments, the antimicrobial product is a household care product. Exemplary house hold care products include, but are not limited to, hard surface cleaners, deodorizers, fabric care compositions, fabric cleaning compositions, manual dish detergents, automatic dish detergents, floor waxes, kitchen cleaners, and bathroom cleaners. In some instances, the antimicrobial product is selected from the group consisting of hard surface cleaners, deodorizers, fabric care compositions, fabric cleaning compositions, manual dish detergents, automatic dish detergents, floor waxes, kitchen cleaners, bathroom cleaners, and combinations thereof.

Yet in other embodiments, the antimicrobial product is a medical device disinfectant.

Still in other embodiments, the amount of compound of Formula I that is present in the antimicrobial product is about 100 ppm or less.

Other aspects of the invention provide a method for reducing the amount of microbe on a surface, said method comprising contacting the surface with an antimicrobial solution comprising an effective amount of a compound of Formula I.

In some embodiments, the microbe comprises vegetative bacteria. In other embodiments, the microbe comprises bacterial spores, mycobacteria, gram-negative bacteria, vegetative gram-positive bacteria, or a combination thereof. In one particular embodiment, the microbe comprises bacterial spores.

Still in other embodiments, the antimicrobial solution further comprises hydrogen peroxide. Typically, the antimicrobial solution comprises at least 40 ppm of α-keto alkylperacid. Alternatively, the antimicrobial solution comprises about 4,000 ppm or less, typically 1,000 ppm or less, often 500 ppm or less, more often 100 ppm or less, and still more often 50 ppm or less amount of the compound of Formula I.

The half-life of compound of Formula I in the antimicrobial solution typically is about 120 days or more, often about 180 days or more, and more often about 360 days or more.

Yet other aspects of the invention provide a method for reducing the number of infectious vegetative bacteria on a substrate comprising contacting the substrate with an antimicrobial solution comprising an effective amount of a compound of Formula I. Other aspects of the invention provide a method for reducing the number of bacterial spores on a substrate comprising contacting the substrate with an antimicrobial solution comprising an effective amount of a compound of Formula I.

Further aspects of the invention provide methods for preventing and/or reducing bacteria-related diseases in a mammal that result from the mammal's contact with a bacteria-infected substrate. Such methods comprise contacting the substrate with a composition comprising a compound of Formula I prior to allowing the mammal to come in contact with the substrate.

Still other aspects of the invention provide an antimicrobial product comprising a compound of Formula I. In some embodiments, the product is a household care product. Within such embodiments, in some cases the house hold care product is selected from the group consisting of hard surface cleaners, deodorizers, fabric care compositions, fabric cleaning compositions, manual dish detergents, automatic dish detergents, floor waxes, kitchen cleaners, bathroom cleaners, and combinations thereof. In other embodiments, the antimicrobial product is selected from the group consisting of hard surface cleaners, deodorizers, fabric care compositions, fabric cleaning compositions, manual dish detergents, automatic dish detergents, floor waxes, kitchen cleaners, bathroom cleaners, and combinations thereof. Antimicrobial products of the invention can be used in a wide variety of settings including, but not limited to, in health care facilities such as hospitals, rehabilitation, assisted living facilities, etc.

In other embodiments, the antimicrobial product is a medical device disinfectant. Still in other embodiments, the antimicrobial product is used as a disinfectant for aseptic filling equipment. Yet in other embodiments, the antimicrobial product is used in an aseptic food processing system. In other embodiments, the antimicrobial product is used as a disinfectant for biofilms in water systems. Still in other embodiments, the antimicrobial product is used as a disinfectant for waste water treatment.

In some embodiments, the amount of compound of Formula I present in the antimicrobial product is about 100 ppm or less. Still in other embodiments, the half-life of a compound of Formula I is at least 20 days.

DETAILED DESCRIPTION OF THE INVENTION

Some aspects of the invention provide α-keto alkylperacids and methods for producing and using the same. As used herein, the terms "α-keto alkylperacid" and "α-keto alkylperoxyacid" are used interchangeably herein and refer to a compound of the formula: HOO—C(=O)—C(=O)—R, or a salt thereof, where R is alkyl of at least two carbon atoms. The term alkyl refers to a saturated linear monovalent hydrocarbon moiety of two to twenty, typically two to ten, and often two to eight carbon atoms or a saturated branched monovalent hydrocarbon moiety of three to twenty, typically three to ten, and often three to eight carbon atoms. Exemplary alkyl group include, but are not limited to, ethyl, n-propyl, 2-propyl, tert-butyl, pentyl, and the like.

Peracids or peroxyacids refer to carboxylic acids in which the acidic —OH group has been replaced by an —OOH group. They are strong oxidizing agents and are generally unstable. They are most often used as oxidizing agents in various chemical reactions. Peroxy acids are generally not very stable even in solution and decompose to their corresponding carboxylic acid and oxygen. Because most peracids decompose relatively quickly under ambient conditions, they are typically not used for any other purposes except in chemical reactions. Even then, many peroxyacids are synthesized just prior to their use. Some peroxyacids, for example, meta-chloroperoxybenzoic acid (MCPBA), are somewhat stable at a lower temperature as long as they are not in a pure form. Pure MCPBA can be detonated by shock or by sparks. It is therefore, commercially sold as a much more stable mixture that is less than 72% pure.

Typically, peroxyacids are prepared by electrolytic oxidation of ordinary carboxylic acids or by using a transition metal catalyst and an oxidizing agent or by using a very strong oxidizing agent. In electrolytic oxidation, typically a high current density must be used to form the peroxyacid in good yield. Such use of a high current density typically increases the cost of producing peroxyacids.

Peroxyacids can also be produced using a transition metal catalyst and an oxidizing agent or simply by using a strong oxidizing agent. Unfortunately, use of a strong oxidizing agent in and of itself creates potentially dangerous conditions and increases the high cost of peroxyacid production. And use of a transition metal catalyst render the resulting peroxyacid often contaminated with the transition metal.

Some methods of the invention for producing α-keto alkylperacids include contacting an α-keto alkylcarboxylic acid or a salt thereof with an oxidizing agent without any significant stirring and under conditions sufficient to produce the α-keto alklperacid. Typically, the reaction condition comprises non-stirring conditions where a mixture of the α-keto alkylcarboxylic acid and the oxidizing agent is simply allow to stand without any stirring. As used herein, unless the context requires otherwise, the term "stir" or "stirring" refers to agitating or act of causing a mixing of the reagents by using an external force such as by using a mechanical stirrer, a magnetic stirrer, a shaker, or any other mechanical, electrical, magnetic, or manual force including simply mixing the reagents manually (e.g., by stirring or shaking).

Surprisingly and unexpectedly, the present inventors have found that by contacting an α-keto alkylcarboxylic acid and an oxidizing agent and letting the mixture stand without any significant mixing, a good yield of the corresponding α-keto alkylperoxyacid can be produced. Generally, the yield of the reaction is at least 5%, typically at least 8%, and often at least 12%.

It should be noted that the yield of the α-keto alkylperoxyacid is affected by a variety of reaction conditions and reagents used. One of the factors influencing the yield of α-keto alkylperoxyacid is the reaction temperature. Generally, the rate of reaction increases as the temperature increases. However, a higher reaction temperature can also increase the yield of side-product(s) and/or decomposition of the α-keto alkylperoxyacid that is formed. Therefore, the reaction temperature is typically kept at about 10° C. or below, often at about 4° C. or below, and more often at about −10° C. or below.

The concentration of the reagents can also affect the rate and the yield of α-keto alkylperoxyacid. The initial concentration of the oxidizing agent is generally about 12 M or less, typically about 7 M or less, and often about 1 M or less.

The reaction time can also affect the yield of α-keto alkylperoxyacid. Typically the reaction time ranges from about 4 hrs to about 12 hrs, often from about 6 hrs to about 8 hrs, and more often from about 10 hrs to about 12 hrs.

Methods of the invention are applicable to a wide variety of α-keto alkylcarboxylic acids. Generally any α-keto alkylcarboxylic acid can be used to produce the corresponding α-keto alkylcarboxylic acid. Exemplary α-keto carboxylic acids include, but are not limited to, α-keto butyric acid, α-keto valeric acid, α-keto hexanoic acid, etc.

Exemplary oxidizing agents that are useful in methods of the invention include, but are not limited to, hydrogen peroxide, barium peroxide, sodium carbonate peroxide, calcium peroxide, sodium perborate, lithium peroxide, magnesium peroxide strontium peroxide, zinc peroxide, potassium superoxide, and the like.

When describing a chemical reaction, the terms "treating", "contacting" and "reacting" are used interchangeably herein, and refer to adding two or more reagents under appropriate conditions to produce the indicated and/or the desired product. It should be appreciated that the reaction which produces the indicated and/or the desired product may not necessarily result directly from the combination of reagents which were initially added, i.e., there may be one or more intermediates which are produced in the mixture which ultimately leads to the formation of the indicated and/or the desired product.

The reaction is generally conducted in an aqueous solution. Other solvents, such as an organic solvent can also be used in addition to or in place of the aqueous solution. Because it is inexpensive and commercially available in an aqueous solution, typically hydrogen peroxide is used as an oxidizing agent.

The ratio of oxidizing agent to α-keto alkylcarboxylic acid typically ranges from about 0.5:1 to about 2:1, often about 2:1 to about 6:1.

While various reaction parameters are disclosed herein, it should be appreciated that the scope of the invention is not limited to these particular reaction parameters.

Utility

While the use of peroxy alkylcarboxylic acids as an oxidizing agent in a chemical reaction is generally known, surprisingly and unexpectedly, the present inventors have discovered that α-keto alkylperoxyacids have particularly useful and potent antimicrobial properties. Accordingly, compounds and compositions or the invention can be used as a disinfectant. As used herein, the term "disinfection" refers to removal, destruction, killing, or reducing of at least a significant portion of a pathogenic microorganism population from a surface of an object. Typically, methods, compounds and compositions of the invention can be used to reduce at least about 90%, often at least about 95%, more often at least about 98%, still more often at least about 99.9% and most often all of the microorganism population from a surface. Moreover, in contrast to most commercial antimicrobial compounds that are used as disinfectants, α-keto alkylperoxyacids have been found to be also effective against bacterial spores.

Disinfection is often done to protect the integrity of bacteriological test results (for example, test done for health screening of patients) and/or to prevent the occurrence and spread of disease resulting from inability to control the pathogenic microorganism population. As used herein, the term "microorganism" includes bacteria, virus, fungi, algae, prion, and other pathogenic organisms known to one skilled in the art. Typically, the term microorganism refers to bacteria. Physical sterilization—for example, applying steam or other gas via pressurized autoclave—is generally not feasible for disinfection of large spaces and surfaces or sensitive medical equipment. In addition, physical sterilization is inapplicable for protecting the integrity of test results. Moreover, physical sterilization cannot be used on delicate or temperature-sensitive instruments and devices.

Human and mammalian health is impacted by the spread of microbial entities at home, school, work and in the environment generally. As stated above, conventional methods of disinfection or cleaning and sanitizing various equipments and areas require very high temperatures up to 185° F. or the use of a relatively harsh antimicrobial compound. Unfortunately, the majority of conventional chemical disinfecting agents are useful for reducing only gram-positive bacteria.

Bacteria found on human skin is typically divided into two groups, namely, resident and transient bacteria. Resident bacteria are Gram-positive bacteria that establish as permanent microcolonies on the surface and outermost layers of the skin. Such bacteria play a fundamental role in preventing the colonization of other, more harmful bacteria and fungi. Transient bacteria are bacteria that are not part of the normal resident of the flora of the skin. Rather, transient bacteria are deposited when airborne contaminated material lands on the skin or when contaminated material is brought into physical contact with such bacteria. Transient bacteria are typically divided into two subgroups: Gram-positive and Gram-negative.

Gram-positive bacteria include pathogens such as *Staphylococcus aureus, Streptococcus pyogenes* and *Clostridium botulinum*. Gram-negative bacteria include pathogens such as *Salmonella, Escherichia coli, Klebsiella, Haemophilus, Pseudomonas aeuginosa, Proteus* and *Shigella dysenteriae*. Gram-negative bacteria are generally distinguished from Gram-positive bacteria via the existence of an additional protective cell membrane in the former, which often results in Gram-negative bacteria being less susceptible to conventional, topical antibacterial actives.

As stated above, there exist several compositions and methods for reducing and/or eliminating the formation of bacteria and/or viruses. For example, it is well known that the washing of hard surfaces, food (e.g., fruit or vegetables) and skin, especially the hands, with antimicrobial or non-medicated soap, is effective against viruses and bacteria. Often removal of the viruses and bacteria is due to the surfactant activity of the soap and the mechanical action of the wash procedure, rather than the function of an antimicrobial agent. Thus, it is recommended that people wash frequently to reduce the spread of viruses and bacteria. However, many conventional products and methods of sanitization, including washing, fail to address the dilemma of sanitization "on the go," that is to say, when a consumer is removed from the benefit of running water. Those skilled in the art have attempted to resolve this dilemma via the incorporation of antimicrobial agents into disinfecting lotions, cleansing wipes and the like. Such articles reduce the need for water during or following the application of the subject composition.

Other conventional antimicrobial cleansing products include deodorant soaps, hard surface cleaners, and surgical disinfectants. These traditional, rinse-off antimicrobial products have been formulated to provide bacteria removal during washing. A few such products, including antimicrobial soaps, have also been shown to provide a residual effectiveness against Gram-positive bacteria, but provide limited residual effectiveness against Gram-negative bacteria. By "residual effectiveness," it is meant that the antimicrobial agent controls microbial growth on a substrate by either preventing growth of microbes or engaging in continuous kill of microbes for some period of time following the washing and/or rinsing process. To address the dilemma of limited residual efficacy against Gram-negative bacteria, some have sought to incorporate high levels of alcohol and/or harsh surfactants into contemporary antimicrobial products, which have been shown to cause dryness and irritation to skin tissues.

While hundreds of different compounds registered with the EPA, claiming to effectively disinfect or sanitize against various microbes, the vast majority, if not all, of the registered compounds have one or more of the following undesirable characteristics: will leave a residue on the treated surface (which must be wiped away); are flammable (thus, considered a DOT hazard material subject to extra transport and storage restrictions and costs); are corrosive, to some degree, to the surfaces to which they are applied; are toxic to animals (human and non-human); and are, thus, not considered environmentally-friendly; a concept that has been coined in many industries, broadly, as being "Green." In particular, the following undesirable characteristics have been identified with various currently-used chemical disinfectants: Ethanol and Isopropanol are slow in their germicidal action on surfaces, fairly ineffective against Gram positive bacteria and are not effective against spores. In addition, these are flammable compounds and require one to follow hazardous shipping requirements. Formaldehyde has a pungently irritating odor and is toxic. Phenols, which are basic to a number of popular disinfectants at high dilutions, are toxic, are flammable, and are not effective in ordinary usage against spores. Quartenary ammonium compounds often leave residues, are neutralized by anionic detergents, and are not tuberculocidal or sporicidal even at high concentrations. Hypochlorites are strong oxidizing agents and may function as disinfectants at the proper concentrations, but are, as a whole, corrosive to metals and can be dangerous to handle. Iodophors likewise may function as disinfectants at the proper concentrations, but leave stains (residue) and are often less effective if any appreciable amount of protein is present. Most heavy metal based antimicrobial agents are toxic and more bacteriostatic than bacteriocidal. Peroxides are widely used to clean skin surfaces and wounds, but they have negligible antimicrobial activity.

Microorganisms, including bacteria, fungi, algae, viruses, prions and other such microbial entities, can be found within any growth condition or environment where life exists. While many varieties of bacterial microbes are useful or 'friendly' to their animal-hosts, others prove irritating and troublesome—yet, relatively harmless—to manage their populations. Many strains of microbes pose a very serious—and often lethal—risk to the health of co-existent animal populations. Decreasing those troublesome, very serious, and lethal microbial populations under non-sterile conditions requires the use of an antimicrobial agent. Different bacteria show varying degrees of resistance toward a particular disinfectant. Prions tend to be the most-resistant of all microbial entities to antimicrobial agents. Bacterial spores and mycobacteria are generally considered to be the most resistant forms of the bacteria, followed by Gram-negative bacteria, which are generally considered to be more resistant than vegetative Gram-positive bacteria such as the staphylococci and enterococci.

Some aspects of the invention provide antimicrobial compositions and methods for using the same. In some embodiments, the antimicrobial compositions include an α-keto alkylperoxyacid. Surprisingly and unexpectedly, the present inventors have discovered that such compositions are also effective in disinfecting bacterial spores. Compositions of the invention can optionally include one or more additional antimicrobial agent (e.g., hydrogen peroxide), a pH neutral diluting solvent (e.g., water), or a combination thereof. Typically, the diluting solvent is a pH neutral liquid solvent adaptable for dissolving the α-keto alkylperoxyacid, e.g., water.

Other aspects of the composition can also include an additional agent that can attack the protective protein layer of microbes (for example, non-enveloped viruses or spores) and/or an additional agent that can dissolve the lipid nature of the envelopes or membranes of the microbes. Suitable additional antimicrobial agents include organic acids, peroxides, alcohols, and ethers.

In some embodiments, the concentration of α-keto alkylperoxyacid in solution is about 1,000 ppm or less, typically 500 ppm or less, often 400 ppm or less, more often 200 ppm or less, and most often 100 ppm or less. Yet in other embodiments, the composition comprises at least about 2.5% (v/v) of α-keto alkylperoxyacids.

As stated above, compositions of the invention can also comprise a second antimicrobial agent. In some cases, the amount of second antimicrobial agent can be at least 3% (v/v). Suitable second antimicrobial agents include those mentioned herein as well as other antimicrobial agents known to one skilled in the art. In one particular embodiment, the second antimicrobial agent is hydrogen peroxide.

Compositions of the invention can also include one or more of the additional agents. Exemplary additional agents include, but are not limited to, organic acids (such as dichloracetic acid for protein disruption), other peroxides (for protein disruption), alcohols (such as diacetone alcohol for membrane disruption), and ethers (such as butylene glycol monomethyl ether for membrane disruption). Compositions of the invention have shown to be generally non-toxic and non-flammable. Compositions of the invention also evaporate relatively rapidly from a surface-of-interest leaving only an acceptable level of measurable residue.

In some embodiments of the invention, compositions of the invention are used to disinfect a gram-positive bacteria, a gram-negative bacteria, a bacterial spore, or a combination thereof. Unlike other conventionally known antimicrobial agents that are commercially used, compositions of the invention have been shown to be effective in not only disinfecting gram-positive bacteria, but also in gram-negative bacteria, and bacterial spores.

In many instances, compositions of the invention provide at least 6-log order complete kill or reduction of vegetative bacteria when applied to a surface. In other instances, compositions of the invention provide at least 5-log reduction of bacterial spores. Often, compositions of the invention provide a "complete kill" of the bacterial population atop the surface such that any functional bacteria remaining atop the surface-of-interest is/are not capable of re-populating to a measureable level, thereby rendering any toxicity or pathogenic functionality of the original bacterial population effectively null.

Compositions of the invention can be applied in aerosol form such as spraying from a bottle containing liquid antimicrobial agent onto a surface. Once applied to the surface, the composition is adapted to evaporate to dryness (to the touch), typically within about 10 to about 30 minutes while leaving acceptable levels (if any) of measureable residue on the surface, such acceptable levels are generally set based on the surface on which the disinfectant is used. Compositions of the invention are typically non-flammable and of very low toxicity allowing them to be shipped as a non-hazardous chemical, per DOT guidelines. Moreover, solutions comprising the compositions of the invention often have low surface tension and are effective in the presence of proteins.

Compositions of the invention can be used to disinfect clean rooms, hospitals, veterinary and dental offices, laboratories (e.g., general medical/veterinary/dental, Q.A. manufacturing, new product development/R&D, and other laboratories), medical equipments and devices, household surfaces, sports equipments, as well as any suitable objects or surface so desired. Some of the characteristics of compositions of the invention include, but are not limited to, effectiveness at high dilutions in the presence of organic matter; a broad spectrum of antimicrobial activity-effectiveness against gram-positive, gram-negative bacteria, spores, viruses, and fungi); stable under the conditions of transport, storage and use; homogeneity; solubility in water, fats, and oils for good penetration into microorganisms; low surface tension for penetration into cracks and crevices; minimum toxicity-lack of acute and chronic toxicity, mutagenicity, carcinogenicity, etc.; capable of being applied with no residue after a desired period of time has passed; pleasant or minimal odor; non-flammable; low or no impact to plants and animals; and low cost.

Other aspects of the invention provide products that comprise the antimicrobial compositions of the present invention, as well as combinations of such products. Indeed, the combined and systematic use of products containing the antimicrobial compositions of the invention serves to eradicate microorganisms for a longer period of time and prevent their spread.

Some embodiments of the invention provide personal care products comprising the antimicrobial compositions disclosed herein. Suitable personal care products comprising the antimicrobial composition disclosed herein include, but are not limited to, hand soaps, hand sanitizers, body washes, mouth washes, toothpastes, shower gels, shampoos, body lotions, deodorants, nasal sprays, foot care, vaginal care and/or wash, pet care and combinations thereof.

In yet other aspects of the present invention, the personal care products disclosed herein take the form of a wipe product, particularly suitable for wiping or drying the face or hands. In such instance, the antimicrobial compositions of the invention are typically embedded or impregnated into the wipe product.

Still in other aspects of the present invention, the personal care product disclosed herein takes the form of a tissue or towel, also suitable for wiping or drying the face or hands. In another aspect of the present invention, the personal care product takes the form of a feminine napkin and/or a diaper. In another aspect of the present invention, the personal care product takes the form of a first aid antiseptic for irritated, injured, or acne-affected skin and/or for pre or post surgical use.

Yet other aspects of the invention provide antimicrobial compositions disclosed herein that are incorporated into one or more household care products. Indeed, suitable household care products for purposes of the invention include, but are not limited to, hard surface cleaners, deodorizers, fabric care compositions, fabric cleaning compositions, manual dish detergents, automatic dish detergents, floor care compositions, kitchen cleaners or disinfectants, bathroom cleaners or disinfectants and combinations thereof.

In other aspects of the invention, the household care product takes the form of a wipe or towel, suitable for household cleaning and/or care. In some embodiments of the invention, the household care products can comprise certain adjunct ingredients. Exemplary adjuncts include, but are not limited to, detersive enzymes, builders, bleaching agents, bleach activators, transitional metal bleach catalysts, oxygen transfer agents and precursors, soil release agents, clay soil removal and/or anti-redeposition agents, polymeric dispersing agents, brightener, polymeric dye transfer inhibiting agents, chelating agents, anti-foam agents, alkoxylated polycarboxylates, fabric softeners, perfumes, carriers, hydrotropes, processing aids, dyes or pigments, solvents for liquid formulations, solid fillers, detersive surfactants and combinations thereof.

Yet still in other aspects of the invention, the antimicrobial compositions disclosed herein can be incorporated into a skin care product. In such aspects of the invention, the skin care product incorporates a dermatologically acceptable carrier to facilitate safe transfer of the antimicrobial composition disclosed herein to the desired area of the skin. In some embodiments, the skin care product can include certain adjunct ingredients. Suitable adjuncts include, but are not limited to, other antimicrobial and antifungal actives, surfactants, desquamation actives, anti-acne actives, anti-wrinkle actives, anti-atrophy actives, anti-oxidants, radical scavengers, chelators, flavonoids, anti-inflammatory agents, anti-cellulite agents, topical anesthetics, tanning actives, sunscreen actives, conditioning agents, thickening agents, detackifying agents, odor control agents, skin sensates, antiperspirants and mixtures thereof. Other suitable adjunct ingredients are well known to one skilled in the art. See, for example, U.S. Pat. No. 6,294,186, which is incorporated herein by reference in its entirety.

Additional objects, advantages, and novel features of this invention will become apparent to those skilled in the art upon examination of the following examples thereof, which are not intended to be limiting. In the Examples, procedures that are constructively reduced to practice are described in the present tense, and procedures that have been carried out in the laboratory are set forth in the past tense.

EXAMPLES

Example 1

This example illustrates one method of testing the antimicrobial effects of compounds of the invention.

Kill Time Test

This is a test performed to demonstrate log reduction values over time for a disinfectant against selected bacteria, fungi, and/or mold. A representative list of the organisms tested include, but are not limited to, *Bacillus subtilis, Bacillus atrophaeus, Bacillus thuringiensis, Staphylococcus aureus, Salmonella cholerasuis, Pseudomonas aeruginosa, Aspergillus niger*, and *Trichophyton mentagrophytes*. The following exemplifies one procedure derived from disinfectant test methods found in guidelines of the Association of Official Analytical Chemists (AOAC) to meet "log reduction criteria" established by the U.S. Environmental Protection Agency (EPA) and U.S. FDA for certain applications: (1) A tube of the sample-disinfectant is placed into a waterbath for temperature control and allowed to equilibrate; (2) Once the tube has reached temperature, it is inoculated to achieve a concentration of approximately $10^6$ CFU/mL; (3) At selected time points (generally five points are used including zero) aliquots are removed and placed into a neutralizer blank; (4) Dilutions of the neutralizer are made and selected dilutions plated onto agar; (5) Colonies are enumerated and log reductions are calculated.

Preparation of Bacterial Suspensions

In order to obtain observable significant reductions (on the order of $10^6$) of surface bacteria, a high number of viable CFU/in$^2$ must be available for treatment on the surface to be disinfected. Since a substantial number of organisms die during the drying process, it is necessary to start with bacterial suspensions that exceed the concentration desired on the final surface. It has been found that a suspension prepared from an agar plate that has been stored refrigerated over-night yields a relatively even surface film upon application and drying. The cool overnight storage of the agar plate reduces the surface tension of the subsequent suspension. Suspensions were prepared in sterile skim milk medium (SM) by harvesting the organism from the agar plate using a sterile cotton swab and vigorously vortex mixing to achieve homogeneity. A viable concentration of $10^8$-$10^9$ CFU/mL was used. Most non-fastidious organism suspensions can be retained in the cooler for several days, and were used as long as enumeration demonstrated satisfactory viability.

Test Surface Preparation

Glass cover slips (e.g., 25 mm$^2$) were used as the test surface for this procedure. Sterile slides were used for this procedure. Slides were sterilized by placing them in layers separated by filter paper (e.g., Whatman #1) and placing them in an aluminum envelope then baking at 150-170° C. for 1-2 hours.

The microorganism film was prepared by dispensing 20 µL of suspension onto a sterile slide and spreading the suspension drop over the surface of the slide. A sterile inoculating needle that has been bent in the shape of a hockey stick was used. The slide were placed on the pins of a sterile disposable plastic 96 well inoculating head that had small drops of sterile water placed onto some of the pins to help hold the slide in place during preparation. The suspension was spread as near to the edges of the slide as possible without touching the edge. The drop was respread once more when necessary without over spreading. The suspension was allowed to dry uncovered at room temperature. Inoculated slides were used as soon as possible, often the same day to minimize loss of viability.

Disinfectant Application

Care was taken during treatment application to assure consistency between slides and experiments. Disinfectants were applied to inoculated slides with an air brush (e.g., Iwata revolution R4500) from a distance of 20-30 cm and a 12-18 psi setting of the compressor output regulator. Travel time for a treatment pass was about 1 ft/sec. Methods were adjusted in order to maintain consistent application between slides. Slides were air dried uncovered at room temperature.

Enumeration

The effectiveness of treatments was evaluated by enumeration of the surviving bacteria on the slide. The bacteria were removed from the slide and the disinfectant was neutralized by immersion of the slide in Letheen broth (LB). The bacteria were then plated in appropriate dilutions. A positive control was included for comparison to assess efficacy.

To enumerate viable organisms on a slide, the slide was placed into a 50 mL centrifuge tube containing 20 mL of LB. The tube was vigorously shaken for 5 seconds and then vortexed for 5 seconds. Mixing step was repeated once. The LB was diluted in peptone, and was plated on an appropriate agar to attain countable dilutions. The LB tube (for decreased limit of quantitation) and agar plates were incubated overnight at the appropriate atmosphere and temperature.

Typically, for an effective disinfectant, about 50 µL of the LB tube was logarithmically spiral plated (DF=20) onto the appropriate agar. In some cases, LB was plated at higher dilutions, e.g., transferred 90 µL of LB to 9 mL of peptone and spiral plated 50 µL (DF=2000).

The CFU/slide was calculated using the spiral plater counting tables and multiplying by the dilution factor. Viability loss due to disinfection was determined by comparing treated slide values with the untreated positive control.

Example 2

Various concentrations of peroxy pyruvic acid generated from different compositions of a mixture from pyruvate, hydrogen peroxide ($H_2O_2$), and water were tested to determine the log reduction of *Bacillus cereus* spores. These spores had been incubated for 7 years and thus the possibility of vegetative cells remaining was very low. Each sample of dilute pyruvate and hydrogen peroxide solution noted in Table 2 was tested employing the spray test outlined above. Slides of MRSA were treated with peroxy pyruvic acid derived from the composition of 10% pyruvate and 3% $H_2O_2$ as a control. The log reduction of the MRSA control was approximately 6-logs, there was no growth in the broth used to plate for enumeration, therefore, it was assumed that complete elimination of the MRSA population was accomplished. As Table 2 illustrates, peroxy pyruvic acid derived from a mixture of 10% pyruvate with 3% $H_2O_2$ resulted in a 3.5-log reduction of the *B. cereus* spores. However, peroxy pyruvic acid derived from the composition of 5% pyruvate and 3% $H_2O_2$ eliminated all the *B. cereus* spores. As in Example 1 above, the water used in these studies is USP purified.

TABEL 2

| Log Reduction of *Bacillus cereus* spores. Positive *B. cereus* Control (BC 2) log = 5.7 Positive MRSA Control (Sta 25) log = 8.3 | | | | |
|---|---|---|---|---|
| Solution No. | Organism | % $H_2O_2$ | % Pyruvate | Log Reduction |
| 2 | MRSA | 3 | 10 | >5.7* |
| 1 | BC 2 | 1 | 10 | 1.1 |
| 2 | BC 2 | 3 | 10 | >3.5 |
| 3 | BC 2 | 1 | 5 | 0.4 |
| 4 | BC 2 | 3 | 5 | 5.7* |
| 5 | BC 2 | — | 10 | 1.1 |
| 6 | BC 2 | — | 5 | 0.8 |

*Total kill/destruction of microbes, i.e. no growth in Letheen broth tubes (3 reps).

Example 3

Peroxy pyruvic acid was synthesized as follows. Pyruvic acid was added to hydrogen peroxide at a temperature of between −30° C. and 10° C. until a conglomerate layer formed on the bottom of the flask. The reaction was allowed to stand without stirring until all pyruvic acid had dissolved into solution. Formation of peroxy pyruvic acid was confirmed by mass spectrometer and by chemical reaction.

Example 4

The reaction of Example 3 was repeated with the addition of Sulfuric Acid ($H_2SO_4$) as a catalyst. An ice bath was used to keep the reaction cool resulting in quantifiable amounts of perpyruvic acid production.

Example 5

Reaction of Examples 3 and 4 were repeated for α-Ketobutanoic Acid ($CH_3CH_2COCOOH$) and α-Ketovaleric Acid ($CH_3CH_2CH_2COCOOH$) to produce the corresponding α-keto peracids.

Example 6

FIG. 1 shows efficacy of peroxy pyruvic acid against *C. Difficile* using sulfuric acid catalysts and methods of Example 1 above. All efficacy studies for *C difficile* were done according to the Official Method 966.04 "Sporicidal Activity of Disinfectants" FIG. 2 shows efficacy of peroxy alpha keto butyric acid against *C. Difficile.*

Example 7

In another experiment, 15 ml of 30% Hydrogen Peroxide was stirred using a stir bar while adding 0.25 ml of the Pyruvic acid in increments every 1.5 minutes. In one instances, the reaction was carried out at room temperature and in another instances at 5° C. Titration of the resulting mixtures showed that there was no observable peracid formation.

Example 8

When preparing Peroxy-alpha-Ketobutyric Acid (POKBA) from alpha-Ketobutyric Acid, some modifications were needed due to the physical nature of the material. Alpha-Ketobutyric Acid is a hygroscopic solid that melts at 30-34° C. Thus, it is often present as a mixture of liquid and solid. The liquid was added first and this initiated the reaction after approximately 10% of the total weight had been added. This was a marked departure from the preparation of peroxypyruvic acid, in which the reaction initiates almost immediatealy with the first addition of the pyruvic acid.

As in the preparation of perpyruvic acid, the hydrogen peroxide was held at about 4° C. When the last of the liquid alpha-Ketobutyric Acid had been added, it becomes necessary to either add a solid or to add a liquid (obtained by immersing the container with the acid into a hot water bath at 50° C. The resultant melt was then added in the same manner as before except that, since a warm liquid was being added to a cold liquid, the additions were made with greater time periods between them so as to allow the temperature to re-equilibrate. In addition, upon contact with the cold liquid some of the melted solid froze, thus causing a small amount of solid to sink to the bottom. This solid reacted and the greater time periods between additions became necessary.

Overall, it is believed that this reaction proceeded somewhat slower than the perpyruvic acid synthesis, although it was essentially complete within a week as in the case with Pyruvic acid when prepared without a catalyst.

Example 9

Pyruvic peracid (PPA) and Peroxy α-ketobutyric acid (POKBA) were tested against *C. difficile* using the ASTM E2197-02 testing method and the results are shown on FIG. 3. As the graph shows, POKBA is significantly more active compared to PPA. The method of testing these molecules against *C. difficile* was designed to evaluate the ability of liquid chemical germicides to inactivate vegetative bacteria, viruses, fungi, mycobacteria and bacterial spores in the presence of a soil load on disk carriers that represent environmental surfaces and medical devices. It was also designed to have survivors that can be compared to a mean of no less than three control carriers to determine if the performance standard has been met: The test protocol did not include any wiping or rubbing action. This test method is a standard test promulgated by ASTM Committee E35 on Pesticides and Subcommittee E35.15 on Antimicrobial Agents. The stringency in the test is provided by the use of a soil load, the microtopography of the carrier surface and the small ratio of disinfectant to surface area (1:5) typical for many disinfectant applications. Thus the formulation under test is presented with a reasonable challenge while allowing for efficient recovery of the test organisms from the inoculated carriers with or without their exposure to the test formulation. The metal disks used in the basic test are also compatible with a wide variety of germicidal actives and most surfaces in consumer based product manufacturing and health care facilities. The design of the metal discs makes it possible to place onto each precisely measured volume of the test organism (28 μL) as well as the test formulation (125 μL). The inoculum is placed at the center of each disk whereas the volume of the test formulation covers nearly the entire disk surface thus eliminating the risk of any organisms remaining unexposed to the test formulation. The relatively small ratio of 1:5 between the volume of the inoculum and that of the test formulation closely reflects many field applications of liquid chemical germicides. In all tests other than those against viruses, the addition of 9.95 mL of a diluent gives a 1:200 dilution of the test formulation immediately at the end of the contact time. While this step in itself may be sufficient to arrest the germicidal activity of most formulations, a Letheen Broth (LB) was used as a specific neutralizer and diluent.

The soil load used in this test was a mixture of three types of proteins (high molecular weight proteins, low molecular weight peptides and mucous material) and consisted of a mixture of 0.5 g of tryptone, 0.5 g of BSA, and 0.04 g of bovine mucin in 10 mL phosphate buffer (pH 7.2). These solutions were prepared separately and sterilized by passage through a 0.22 μm pore diameter membrane filter, aliquoted and stored at either 4° C. or −20° C. To obtain 500 μL of the inoculum for the discs, 340 μL of the microbial suspension was added to 25 μL of BSA, 100 μL of mucin, and 35 μL of tryptone stock.

Stainless Steel Disks (1 cm in Diameter and Approx. 0.7 mm Thick) were prepared from sheets of magnetized and brushed stainless steel 10 similar to that used in the manufacture of countertops. The disks were soaked in a detergent solution for at least one hour to degrease them and then washed and sterilized by autoclaving.

C. difficile was prepared by suspending a C. difficile suspension overnight into pre-reduced Brain heart infusion broth (BHI) and allowed to grow overnight. Inoculates from the BHI were streaked onto the surface of a sufficient number of pre-reduced trypticase soy agar plates with 5% sheep blood (BA) for confluent growth using a swab wetted in the prepared suspension (i.e., containing 1 mL of spore suspension). The BA plates were incubated for 14-28 days anaerobically. Afterwards, the cells were harvested from the agar by adding 3 mL of sterile distilled water to the surface of the BA plate and suspended using a bent glass rod to suspended the cells from the plate into the water. A combined rinsing of each plate was added into one or more 50 mL centrifuge tube(s). The cells were centrifuged at 4500 rcf for 15 minutes and the supernatant carefully discarded. These steps were repeated two additional times. The final 10 mL of spore suspension was heated in a 65-70° C. water bath (assuring the entire tube is immersed) for 30 minutes. The final concentration of spores in the suspension were checked for the purity of the spores by preparing a 1:1000 dilution in anaerobic broth and spiral plating 50 μL onto reduced BA plates. The spores were stored at 2-8° C. until needed.

The disks were inoculated with 25 μl, of $10^6$ C. difficile spores suspended in the soil load and allowed to dry. Afterwards, 125 μL of different concentrations of the alpha Keto peroxy acids (AKPA) were added to the discs and allowed to set for 10 minutes before dilution into the LB neutralizer. Afterwards, the LB neutralizer was vortexed for 5 seconds and 50 μL of the LB in the tube was logarithmically spiral plated (DF=20) onto the appropriate agar. Controls were treated similarly as with the AKPA with the exception that water replaced the AKPA.

Example 10

Figure 1:
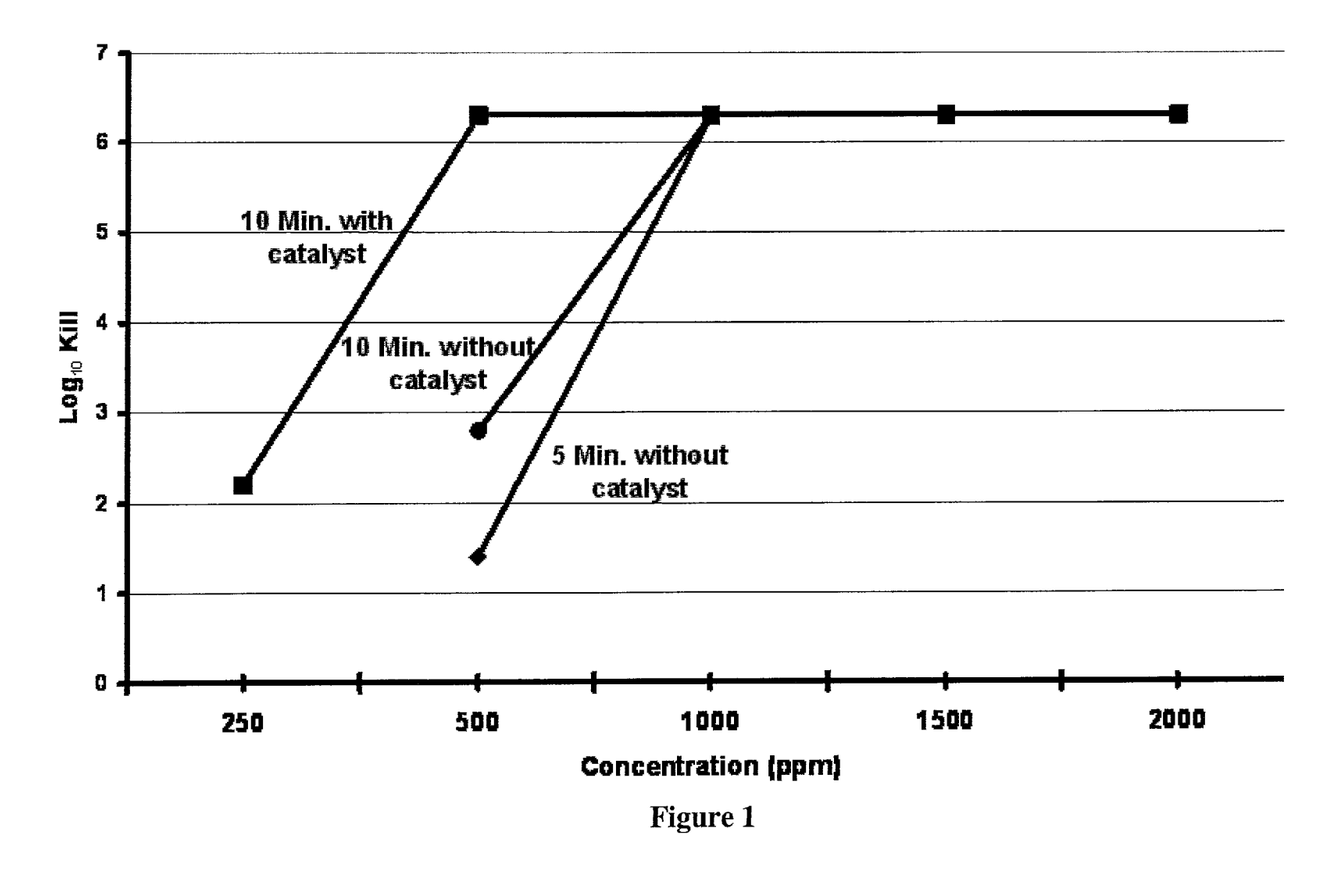
FIG. 1 shows graph of efficacy of peroxy α-keto pyruvic acid against *C. difficile* with or without a catalyst.
Figure 2:
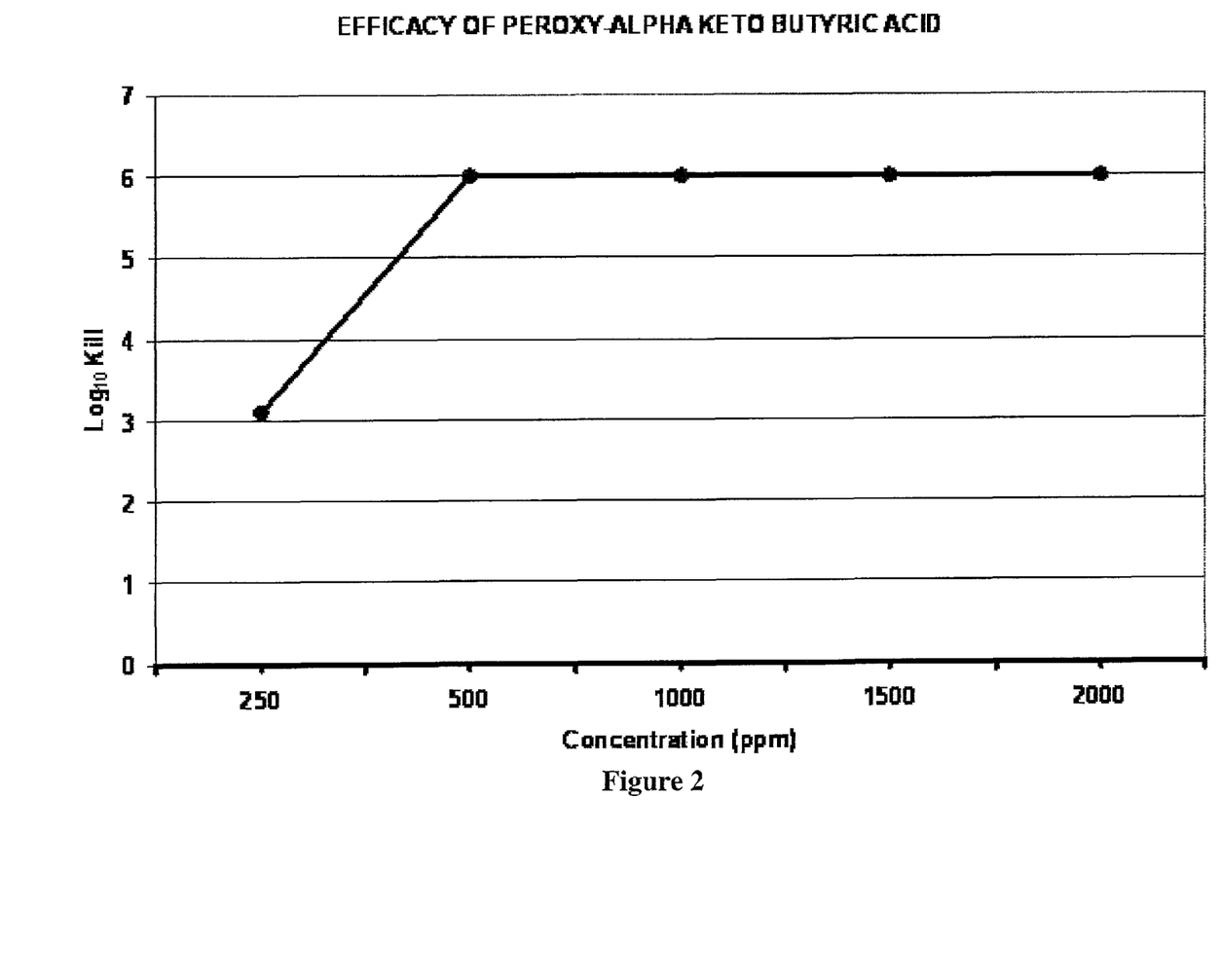
FIG. 2 is a graph showing efficacy of peroxy α-keto butyric acid against *C. difficile* at various concentrations.
Figure 3:
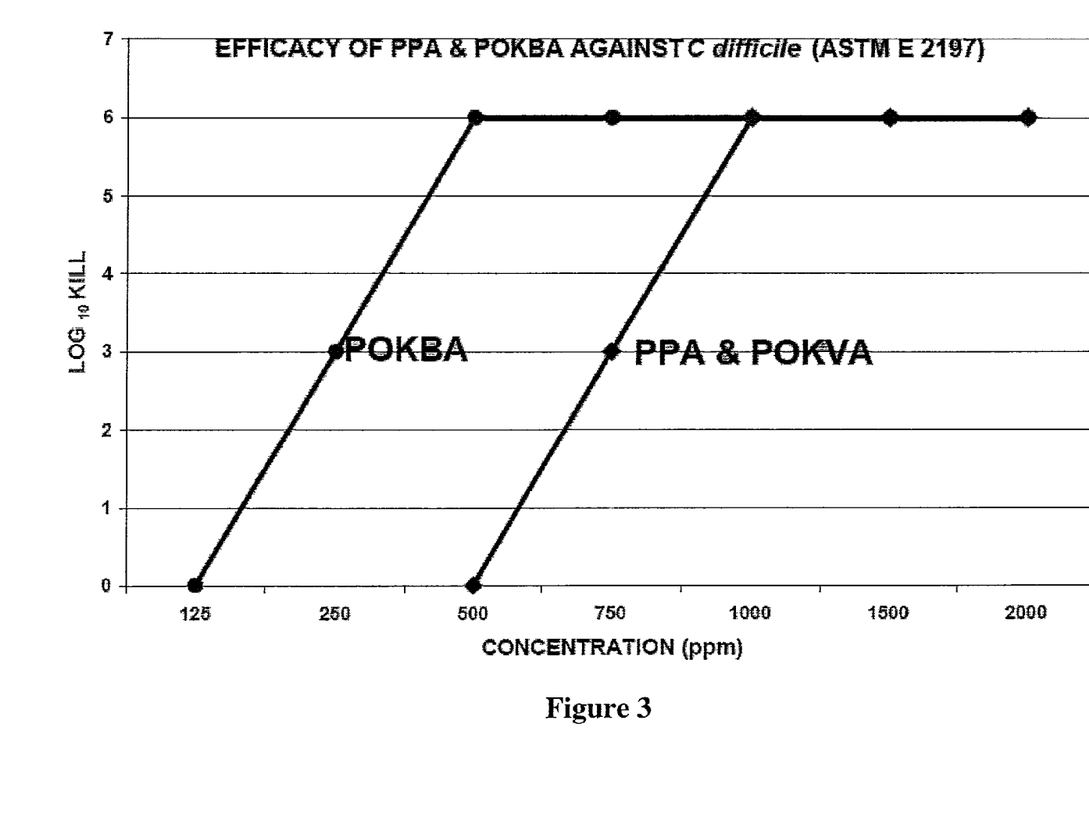
FIG. 3 is a graph showing comparison of effectiveness against *C. difficile* between peroxy pyruvic acid and peroxy α-ketobutyric acid.
Figure 4:
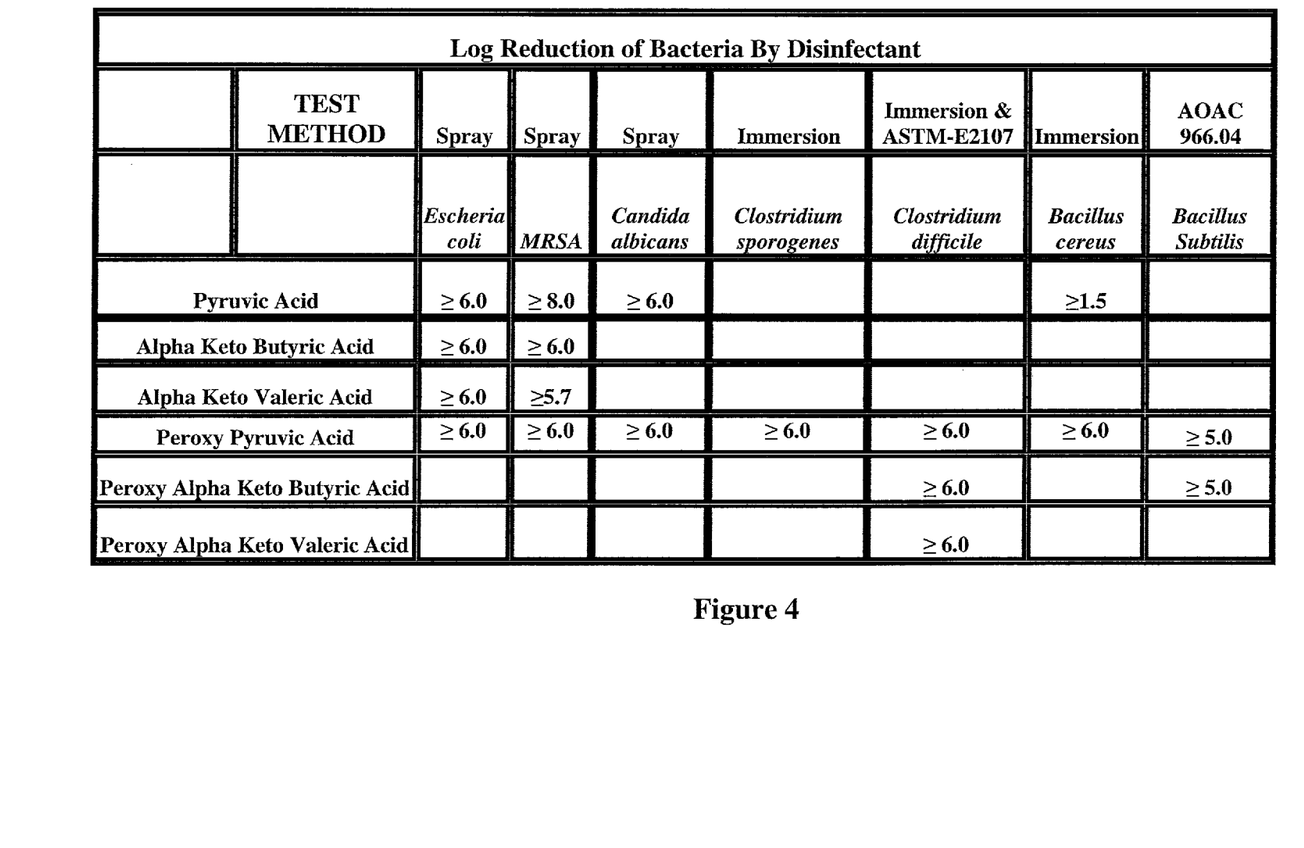
FIG. 4 is a table showing effectiveness of antimicrobial activities of various carboxylic acids and peroxy α-keto carboxylic acids against various microorganisms.

Various carboxylic acids and peroxy α-keto carboxylic acids were tested against various microorganisms. The results are shown in FIG. 4. A series of methods were used for testing the microbes and are defined by the column titles on the Table in FIG. 4. The details of these methods are as follows:

Preparation of Bacterial Suspensions

In order to obtain observable significant reductions (on the order of $10^6$) of surface bacteria, a high number of viable CFU/in² must be available for treatment on the surface to be disinfected. Since a substantial number of organisms die during the drying process, it is necessary to start with bacterial suspensions that exceed the concentration desired on the final surface. It has been found that a suspension prepared from an agar plate that has been stored refrigerated overnight yields a relatively even surface film upon application and drying. The cool overnight storage of the agar plate reduces the surface tension of the subsequent suspension. Suspensions were prepared in sterile skim milk medium (SM) by harvesting the organism from the agar plate using a sterile cotton swab and vigorously vortex mixing to achieve homogeneity. A viable concentration of $10^8$-$10^9$ CFU/mL is typically used. Most non-fastidious organism suspensions can be retained in the cooler for several days, and used as long as enumeration demonstrates satisfactory viability. Spore suspensions can be used directly or diluted to achieve the desired concentration of organism.

Test Surface Preparation

Sterile glass cover slips (e.g., 25 mm²) were used as the test surface for the spray test and the immersion test. Slides were Sterilized by placing them in layers separated by filter paper (e.g., Whatman #1) and then in an aluminum envelope and baking them at 150-170° C. for 1-2 hours.

The organism film on the slide was prepared by dispensing 20 μL of suspension onto a sterile slide and spreading the suspension drop over the surface of the slide. With a sterile inoculating needle that has been bent in the shape of a hockey stick. Sometimes it is helpful to rest the slide on the pins of a sterile disposable plastic 96 well inoculating head that has had small drops of sterile water placed onto some of the pins to help hold the slide in place during preparation. The suspension was spread as near to the edges of the slide as possible without touching the edge. Care was taken to not allow organisms onto the reverse side of the slide, as it will not be exposed to disinfectant when treated. The suspension was allowed to dry uncovered at room temperature. The Inoculated slides were used the same day as prepared to minimize loss of viability.

Spray Test

Disinfectants were applied to inoculated glass coverslips with an air brush (e.g., Iwata revolution R4500) from a distance of 20-30 cm and a 12-18 psi setting of the compressor output regulator. Travel time for a treatment pass was ~1 ft/second. Treated slides were air dried uncovered at room temperature.

Immersion Test.

Organisms were prepared on slides as indicated above. The carrier slides with the organisms were placed in 20±2 mL of disinfectant and allow to soak for the desired amount of time. After 10 minutes, the carrier slides were placed into LB broth and enumerate discussed below.

Organism Enumeration

The effectiveness of treatments were evaluated by enumeration of the surviving bacteria on the slide versus positive controls which had been treated with water. The positive controls demonstrated how many surviving bacteria were on the carrier slides when not treated with disinfectant. The bacteria are neutralized and removed from the slides by votexing them in Letheen broth (LB) and then plating for counts by pipetting 50 μL of the appropriate dilutions in the LB tubes onto a plate and logarithmically spiral plating (DF) onto the appropriate agar. Also direct dilution of the original suspension was directly enumerated to determine if there were any viability loss in the organism suspension due to desiccation.

AOAC 966.04 Test Against B. Subtilis

This test is applicable to testing germicides for presence or absence of sporicidal activity against specified spore forming bacteria in various situations and potential efficacy as sterilizing agent. The organism typically used for testing disinfectants for use against bacteria and bacterial spores with medical devices such as endoscopes, catheters, and etc. is B. Subtilis spores because they are known to form biofilms which are difficult to eradicate. This is done by testing the disinfectants for sporicidal kill of the spores which are attached to ceramic penny cylinders.

The *B. Subtilis* spores were formed by inoculating nutrient agar (NA) slants and then washing growth on the slants with 10 mL of sterile deionized water and transferring to Roux bottles containing antibiotic medium #2 (AM#2) with $MnSO_4$. The bottles were placed in a water bath at 65-70° C. water bath for 30 min. Afterwards the spore suspension was centrifuged at ~4500 rpm for 15 min. The supernatant was decanted and the spores resuspended with ~20 mL of sterile water. The centrifugation and resuspension of the spores was repeated 3× more with intermittent homogenization. Finally the *B. subtilis* spore pellet was placed in a 65-70° C. water bath for 30 min then resuspended in 30 mL of sterile water. Afterwards, the suspension was streaked onto nutrient agar for determination of purity.

Evaluation of disinfectants against *B. subtilis* was done by attaching the spores to Porcelain cylinders, 8±1 mm od, 6±1 mm id, 10±1 mm long which had been sterilize by incubation for 2 h in 180° C. air oven. Afterwards the penny cylinders were washed with Triton X-100 and rinsed with water 4 times. The contaminated spores were gently placed into the disinfectant in test tubes for 10 minutes and then removed and placed into 10 mL±0.1 mL of LB neutralizer. The neutralizer tubes were sonicated for 5±1 minute in a room temperature water bath. Afterwards, the tube containing penny cylinders were vortexed and diluted for enumeration by the above described method. Positive controls were penny cylinders that had only been exposed to sterile water.

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/ or equivalent structures, functions, ranges or steps are disclosed herein, and without intending to publicly dedicate any patentable subject matter.

What is claimed is:

1. A product for reducing the number of pathogens on a health care hard surface comprising a peroxy α-ketocarboxylic acid.

2. The product of claim 1, wherein the peroxy α-ketocarboxylic acid is selected from the group consisting of peroxy pyruvic acid, peroxy α-ketobutyric acid, peroxy α-ketovaleric acid, or combination thereof.

3. The product of claim 1, wherein the product further comprises an antimicrobial agent.

4. The product of claim 1, wherein the product further comprises an antifungal agent.

5. The product of claim 1, wherein the product further comprises hydrogen peroxide.

6. The product of claim 1, wherein the product further comprises an alcohol.

7. The product of claim 1, wherein the product further comprises a surfactant.

8. The product of claim 1, wherein the product further comprises an organic acid.

9. The product of claim 1, wherein the product is in the form of a wipe.

10. The product of claim 1, wherein the product is in the form of a spray.

11. The product of claim 1, wherein the product is in the form of a liquid.

12. The product of claim 1, wherein the product is in the form of a gel.

13. A method for reducing the number of pathogens on a health care hard surface comprising contacting the health care hard surface with a composition comprising an effective amount of a peroxy α-ketocarboxylic acid.

14. The method of claim 13, wherein the peroxy α-ketocarboxylic acid is selected from a group consisting of peroxy pyruvic acid, peroxy α-ketobutyric acid, peroxy α-ketovaleric acid, or combination thereof.

15. The method of claim 13, wherein the health care hard surface is located in a hospital.

16. The method of claim 13, wherein the health care hard surface is located in a rehabilitation facility.

17. The method of claim 13, wherein the health care hard surface is located in an assisted living facility.

18. The method of claim 13, wherein the composition penetrates into cracks and crevices of the substrate.

19. The method of claim 13, wherein the pathogen is selected from a group consisting of bacterial spores, mycobacteria, enveloped/non-enveloped viruses, gram-negative bacteria, gram-positive bacteria, fungi, prions, or a combination thereof.

20. The method of claim 13, further comprising allowing the substrate to dry.

* * * * *